United States Patent
Chung et al.

(10) Patent No.: US 9,519,006 B2
(45) Date of Patent: Dec. 13, 2016

(54) HYBRID MICROPROBE FOR ELECTROCHEMICAL AND SERS MONITORING, SCANNING AND FEEDBACK STIMULATION AND THE PREPARATION METHOD THEREOF

(75) Inventors: Taek Dong Chung, Seoul (KR); Beom Jin Kim, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 490 days.

(21) Appl. No.: 14/007,824

(22) PCT Filed: Mar. 29, 2011

(86) PCT No.: PCT/KR2011/002130
§ 371 (c)(1),
(2), (4) Date: Sep. 26, 2013

(87) PCT Pub. No.: WO2012/133961
PCT Pub. Date: Oct. 4, 2012

(65) Prior Publication Data
US 2014/0014507 A1    Jan. 16, 2014

(51) Int. Cl.
*G01Q 70/16*    (2010.01)
*G01Q 60/60*    (2010.01)
(Continued)

(52) U.S. Cl.
CPC ............ *G01Q 70/16* (2013.01); *G01N 21/658* (2013.01); *G01Q 30/02* (2013.01); *G01Q 60/60* (2013.01);
(Continued)

(58) Field of Classification Search
CPC ........ G01Q 70/16; G01Q 30/02; G01Q 60/60; G01N 21/658; H01J 2237/2803; B82Y 35/00; B82Y 15/00
See application file for complete search history.

(56) References Cited

U.S. PATENT DOCUMENTS

2005/0017171 A1    1/2005    Samuelson et al.
2007/0114457 A1    5/2007    Han et al.

FOREIGN PATENT DOCUMENTS

JP    2006-090715 A    4/2006
JP    2010-066140 A    3/2010
(Continued)

OTHER PUBLICATIONS

L. Piao, et al. "Single gold microshell tailored to sensitive surface enhanced Raman scattering probe" Analytical Chemistry, vol. 82, No. 1, Jan. 1, 2010, p. 447-451.*
(Continued)

*Primary Examiner* — J. Christopher Ball
(74) *Attorney, Agent, or Firm* — Alston & Bird LLP

(57) ABSTRACT

The present disclosure relates to a probe capable of electrochemical and Raman spectroscopic monitoring wherein a Raman-active gold microshell having conductivity is attached to the tip of a glass microcapillary tube in which a conductive material is coated on an inner wall thereof by electroless plating. By coupling the probe with a system capable of moving the probe, the activities of various catalyst materials can be detected quickly and information of intermediate products moving from and adsorbed on the surface can be provided.

20 Claims, 7 Drawing Sheets

(51) Int. Cl.
*G01N 21/65* (2006.01)
*G01Q 30/02* (2010.01)
*B82Y 15/00* (2011.01)
*B82Y 35/00* (2011.01)

(52) U.S. Cl.
CPC ............... *B82Y 15/00* (2013.01); *B82Y 35/00* (2013.01); *H01J 2237/2803* (2013.01)

(56) References Cited

FOREIGN PATENT DOCUMENTS

| KR | 10-2006-0058085 A | 5/2006 |
| KR | 10-0697323 B1 | 3/2007 |
| KR | 10-2009-0026933 A | 3/2009 |

OTHER PUBLICATIONS

International Search Report for Application No. PCT/KR2011/002130 dated Oct. 12, 2011.

\* cited by examiner

Images of optical microscope, scale bar = 5 μm

HYBRID MICROPROBE FOR ELECTROCHEMICAL AND SERS MONITORING, SCANNING AND FEEDBACK STIMULATION AND THE PREPARATION METHOD THEREOF

CROSS-REFERENCE TO RELATED APPLICATIONS

This application is a national stage application filed under 35 U.S.C. 371 of International Application No. PCT/KR2011/002130, filed Mar. 29, 2011.

TECHNICAL FIELD

The present disclosure relates to a new monitoring method, system configuration and method for preparing a probe capable of acquiring not only electrochemical information but also spectroscopic information at the same time by improving the existing methodology and system based on scanning electrochemical microscopy (SECM).

BACKGROUND ART

To elucidate the processes that have been industrially employed from long ago at the atomic and molecular level is becoming more important with regard to new energy resources. This has become possible with the invention of scanning tunneling microscopy (STM) which allows observation at the atomic level. The inventors of STM won the Nobel Prize in 1986. Since then, more advanced scanning probe microscopy (SPM) techniques have been developed and it has become possible to investigate not only the surface morphology but also physical and chemical properties using various probes. In 1989, A. J. Bard et al. proposed a scanning electrochemical microscopy (SECM) technique using a small and movable electrochemical probe called an ultramicroelectrode (UME) as a new-concept probe. Since it enables not only observation of the surface morphology but also monitoring the electrochemical reactions occurring on the surface, it is widely used in electrochemical researches on various interfaces.

The probe having microscopic spatial resolution is useful in finding out surface defects resulting from chemical reactions occurring on interfaces such as corrosion or dissolution. Also, it is useful in developing new catalyst materials since it allows fast evaluation of many materials having catalytic activity. For example, development of a new catalyst material for effectively improving the performance of a fuel cell which converts the chemical energy from a fuel into electricity is industrially invaluable since it can replace the expensive platinum catalyst. In addition, the probe may be used to investigate the mechanism and rate of reactions occurring on interfaces. Accordingly, by establishing the condition of ideal catalyst materials through studies on the mechanism of various catalytic reactions, the SECM technique will provide a basis for systematic catalyst development, beyond the existing catalyst development based on limited information.

However, the problems including limitation only to electrochemically active materials, applicability only to materials that can be desorbed from the electrode surface and diffuse into the solution phase, failure to provide information other than electrochemical data, or the like have greatly limited the application of SECM industrially and the SECM technique remains only as a research tool. If the SECM technique can be improved into a system capable of providing chemical information of materials involved in electrochemical reactions in real time, it will be used in various applications. The best way to achieve it is to develop a probe capable of providing not only electrochemical information but also spectroscopic information. The existing SECM probe provides electrochemical information only and cannot provide information about intermediates present on the surface. However, considering that most electrochemical reactions occur in water, spectroscopic measurement is extremely restricted due to absorption by water itself. Raman spectroscopy is one of few methods that can be used in water without a special device and it can be widely used to provide chemical information about electrochemical reactions. However, because the signals from Raman spectroscopic measurement are usually very weak in intensity, only the surface-enhanced Raman scattering (SERS) technique is practically applicable. The SERS phenomenon is found only in specific materials and structures and it is impossible to obtain Raman spectra for electrochemical reactions occurring on electrodes made of arbitrary materials. If a device capable of obtaining Raman spectra, regardless of the material of the electrode on which an electrochemical reaction of interest is occurring, is coupled with the existing SECM technique, it will make a useful analysis tool in many applications including catalyst development.

DISCLOSURE

Technical Problem

The present disclosure is directed to providing a probe capable of reproducibly providing electrochemical and spectroscopic information at the same time regardless of surface material. The present disclosure is also directed to providing a scanning system capable of monitoring not only diffusing intermediate products but also intermediate products moving and adsorbed on the surface.

Technical Solution

In one general aspect, the present disclosure provides a method for preparing a probe, including (a) preparing a metallic microshell by coating a first metallic material on the surface of a spherical template, (b) preparing a conductive capillary tube by coating a conductive material on the inner wall of a capillary tube, (c) trapping the metallic microshell in a tip of the conductive capillary tube and (d) coating a second metallic material on the inner wall of the conductive capillary tube wherein the metallic microshell is trapped.

In an exemplary embodiment, the template may be selected from polystyrene, poly(methyl methacrylate), silica ($SiO_2$) and a mixture thereof, but is not limited thereto. The first metallic material may be selected from Au, Ag, Pt, Pd, Cu and a mixture thereof. The conductive material may be selected from Ru, Pt, Cu, Co, Ni and a mixture thereof and the second metallic material. But, it may be any conductive material that can be deposited by atomic layer deposition, without being limited thereto. Those skilled in the art will easily select the conductive material that can be deposited by atomic layer deposition based on the present disclosure.

In another exemplary embodiment, the second metallic material may be selected from Au, Ag, Pt, Pd, Cu and a mixture thereof, but is not limited thereto. The second metallic material may be identical to or different from the first metallic material. However, it is desired that the second metallic material is identical to the first metallic material so as to exhibit high electrical conductivity by physically binding with the first metallic material.

In another exemplary embodiment, the metallic microshell may have a diameter of 1-3 µm, specifically 1.5-2.5 µm, more specifically 1.8-2.3 µm, most specifically 2 µm, in order to maximize visibility, transportability and SERS property. And, the tip of the capillary tube should be smaller than the diameter of the metallic microshell for the microshell to be attached to the capillary tube. In particular, the diameter of the tip of the capillary tube may be 50-99% of the diameter of the metallic microshell.

In another exemplary embodiment, (a) may be performed by electroless plating using (i) a precursor of the first metallic material selected from potassium tetrachloroaurate hydrate, sodium tetrachloroaurate hydrate, chloroauric acid, hydrogen hexachloroplatinate(IV) hydrate, silver nitrate and a mixture thereof and (ii) a first reducing agent selected from formaldehyde, ascorbic acid, hydroquinone, ammonium hydroxide and a mixture thereof. In particular, (a) may be performed by repeating the electroless plating 2-20 times, more specifically 5-15 times, further more specifically 8-12 times, such that SERS activity and Raman effect can be exerted by the metallic microshell. For the SERS activity or Raman effect to be exerted, a layer of the metallic material should be covered on the entire surface and should have a certain degree of roughness. These conditions may not be satisfied if the amount of the electroless plated first metallic material layer is too small or too large.

In an exemplary embodiment, (b) may be performed by atomic layer deposition at 250-350° C. under a pressure of 1-5 Torr using a precursor selected from bis(ethylcylcopentadienyl)ruthenium, a halide compound (especially, a chloride compound) of the conductive material, an alkyl or alkoxide compound of the conductive material, an organometallic compound such as a cyclopentadienyl complex or an alkyl or silyl amide and a mixture thereof.

In another exemplary embodiment, (c) may be performed by applying a negative pressure to the capillary tube.

In particular, (c) may be performed in a solution of a precursor of the second metallic material selected from potassium tetrachloroaurate hydrate, sodium tetrachloroaurate hydrate, chloroauric acid, hydrogen hexachloroplatinate (IV) hydrate and a mixture thereof. More specifically, a part of the solution of the precursor of the second metallic material may be sucked into the capillary tube during the process. Most specifically, only the precursor of the second metallic material may exist in the capillary tube, without other metallic material or reducing agent.

In another exemplary embodiment, (d) may be performed by electroless plating using (i) a precursor of the second metallic material selected from potassium tetrachloroaurate hydrate, sodium tetrachloroaurate hydrate, chloroauric acid, hydrogen hexachloroplatinate(IV) hydrate and a mixture thereof and (ii) a second reducing agent selected from potassium ferrocyanide ($K_4[Fe(CN)_6]$), ruthenium(II) hexamine chloride, iridium(III) chloride and a mixture thereof.

Specifically, (d) may be performed in a solution of the second reducing agent. In particular, (c-1) diluting the solution of the precursor of the first metallic material and (c-2) adding a second reducing agent or a solution thereof to the diluted solution of the precursor of the first metallic material may be included between (c) and (d). All of (c), (c-1), (c-2) and (d) may be performed with the capillary tube disposed in a solution in order to ensure good attachment of the microshell to the capillary tube.

One of the purposes of the dilution is to replace the solution outside the capillary tube with the solution of the second reducing agent in the state where the metallic microshell is trapped. If the capillary tube is exposed out of the solution, the trapped metallic microshell may be detached from the capillary tube due to surface tension of the solution. Accordingly, the solution outside the capillary tube is replaced in the state where the metallic microshell is trapped. The replaced second reducing agent can induce reduction of the second metallic material on the surface of the microshell trapped in the capillary tube, without having to be in direct contact with the precursor of the second metallic material inside the capillary tube, by donating an electron to the precursor of the second metallic material. It is because, since the first metallic material layer of the microshell is conductive, the second reducing agent can feel the potential of the precursor of the second metallic material and thus the electron can move along the first metallic material layer according to the potential difference generated.

In this aspect, the dilution may be performed until a sufficient difference in concentration of the second metallic material is formed inside and outside the capillary tube. As used herein, "sufficient difference in concentration" refers to a degree whereby the electron donated by the second reducing agent can move along the first metallic material layer and achieve electroless plating inside the capillary tube.

In another general aspect, the present disclosure provides a probe including (i) a capillary tube and (ii) a metallic microshell attached to a tip of the capillary tube.

A conductive material may be coated on the inner wall of the capillary tube, the metallic microshell may include a first metallic material coated on the surface of a spherical template, and the conductive material and the first metallic material may be electrically connected at a region where the metallic microshell is attached to the capillary tube.

A second metallic material may be coated on a layer of the first metallic material of the metallic microshell, which is exposed in the tip of the capillary tube to which the metallic microshell is attached, so as to ensure attachment of the metallic microshell to the capillary tube and to greatly improve the electrical conductivity of the probe.

As described above, the template may be selected from polystyrene, poly(methyl methacrylate), silica and a mixture thereof, the first metallic material may be selected from Au, Ag, Pt, Pd, Cu and a mixture thereof, the conductive material may be selected from Ru, Pt, Cu, Co, Ni and a mixture thereof and the second metallic material may be selected from Au, Ag, Pt, Pd, Cu and a mixture thereof.

The metallic microshell may have a diameter of 1-3 µm and the tip of the capillary tube may have a diameter corresponding to 50-99% of the diameter of the metallic microshell.

The first metallic material may be coated on the spherical template such that SERS activity and Raman effect can be exerted by the metallic microshell. For this, the first metallic material may be coated on the spherical template by repeating electroless plating 2-10 times such that SERS activity and Raman effect can be exerted by the metallic microshell.

In another aspect, the present disclosure provides a method for preparing a probe, including: (A) preparing a metallic microshell by coating a first metallic material on the surface of a spherical template; (B) preparing a capillary tube including a conductive material inside thereof; (C) coating a second metallic material on a tip of the capillary tube; and (D) attaching the metallic microshell to the second metallic material.

In an exemplary embodiment, the template may be selected from polystyrene, poly(methyl methacrylate), silica (SiO$_2$) and a mixture thereof, but is not limited thereto. The first metallic material may be selected from Au, Ag, Pt, Pd, Cu and a mixture thereof. The conductive material may be selected from Ru, Pt, Cu, Co, Ni and a mixture thereof and the second metallic material. But, it may be any conductive material that can be deposited by atomic layer deposition, without being limited thereto. Those skilled in the art will easily select the conductive material that can be deposited by atomic layer deposition based on the present disclosure.

In another exemplary embodiment, the second metallic material may be selected from Au, Ag, Pt, Pd, Cu and a mixture thereof, but is not limited thereto. The second metallic material may be identical to or different from the first metallic material. However, it is desired that the second metallic material is identical to the first metallic material so as to exhibit high electrical conductivity by physically binding with the first metallic material.

In another exemplary embodiment, the metallic microshell may have a diameter of 1-3 μm, specifically 1.5-2.5 μm, more specifically 1.8-2.3 μm, most specifically 2 μm, in order to maximize visibility, transportability and SERS property. And, the tip of the capillary tube should be smaller than the diameter of the metallic microshell for the microshell to be attached to the capillary tube. In particular, the diameter of the tip of the capillary tube may be 50-99% of the diameter of the metallic microshell.

In another exemplary embodiment, (A) may be performed by electroless plating using (i) a precursor of the first metallic material selected from potassium tetrachloroaurate hydrate, sodium tetrachloroaurate hydrate, chloroauric acid, hydrogen hexachloroplatinate(IV) hydrate, silver nitrate and a mixture thereof and (ii) a first reducing agent selected from formaldehyde, ascorbic acid, hydroquinone, ammonium hydroxide and a mixture thereof. In particular, (A) may be performed by repeating the electroless plating 2-20 times, more specifically 5-15 times, further more specifically 8-12 times, such that SERS activity and Raman effect can be exerted by the metallic microshell. For the SERS activity or Raman effect to be exerted, a layer of the metallic material should be covered on the entire surface and should have a certain degree of roughness. These conditions may not be satisfied if the amount of the electroless plated first metallic material layer is too small or too large.

In an exemplary embodiment, (B) may be performed by stretching a glass tube including a metal wire.

In another general aspect, the present disclosure provides a probe including: (i) a capillary tube including a conductive material inside thereof; (ii) a metallic microshell including a first metallic material coated on the surface of a spherical template and attached to a tip of the capillary tube; and (iii) a second metallic material disposed between the capillary tube and the metallic microshell, wherein the conductive material and the first metallic material are electrically connected via the second metallic material.

As described above, the template may be selected from polystyrene, poly(methyl methacrylate), silica and a mixture thereof, the first metallic material may be selected from Au, Ag, Pt, Pd, Cu and a mixture thereof, the conductive material may be selected from Ru, Pt, Cu, Co, Ni and a mixture thereof and the second metallic material may be selected from Au, Ag, Pt, Pd, Cu and a mixture thereof.

The metallic microshell may have a diameter of 1-3 μm and the tip of the capillary tube may have a diameter corresponding to 50-99% of the diameter of the metallic microshell.

The first metallic material may be coated on the spherical template such that SERS activity and Raman effect can be exerted by the metallic microshell. For this, the first metallic material may be coated on the spherical template by repeating electroless plating 2-10 times such that SERS activity and Raman effect can be exerted by the metallic microshell.

Advantageous Effects

The present disclosure presents a new method for reproducibly preparing an ultramicroelectrode (UME) using a gold shell with a known area (dimension) as an electrode. By using the gold shell which gives the strongest Raman signal, the present disclosure can provide not only electrochemical information but also spectroscopic information at the same time. Further, by coupling with a system capable of moving the electrode very close in the z-axis, not only diffused products resulting from surface reactions but also intermediate products moving from and adsorbed on the surface, which could not be observed by scanning electrochemical microscopy (SECM), can be monitored Raman spectroscopically even when they are not Raman-active materials.

DESCRIPTION OF DRAWINGS

In FIGS. 2a and 2b, 1 is an image of a glass microcapillary tube stretched to a such a size that a microshell can be attached, 2 is an image of the glass microcapillary tube wherein an inner wall is coated with a conductive material, 3 shows a schematic view of a process whereby a gold microshell is trapped by the coated glass microcapillary tube and an image of a gold ball trapped by the glass microcapillary tube, and 4 shows a schematic view and an image of a electroless plating process for completely attaching the gold microshell to the tip of the glass microcapillary tube without application of a negative pressure.

MODE FOR INVENTION

In order to obtain electrochemical and spectroscopic information about a surface regardless of the material thereof, a probe itself has to be designed to be capable of obtaining electrochemical and spectroscopic information. For this, the inventors of the present disclosure have prepared a gold shell that exhibits the highest surface-enhanced Raman scattering (SERS) effect by precisely electroless plating gold, which is suitable to achieve the SERS effect, on a polymer ball, which was then attached to the tip of a glass microcapillary tube having an inner wall coated with a conductive film to achieve a physical and electrical contact so that the gold shell can be used as an electrode. The gold microshell probe was coupled with a system capable of precise scanning along the z-axis so as to allow obtainment of spectroscopic information of intermediate products moving from and adsorbed on reaction surface.

EXAMPLE

Figure 1A:
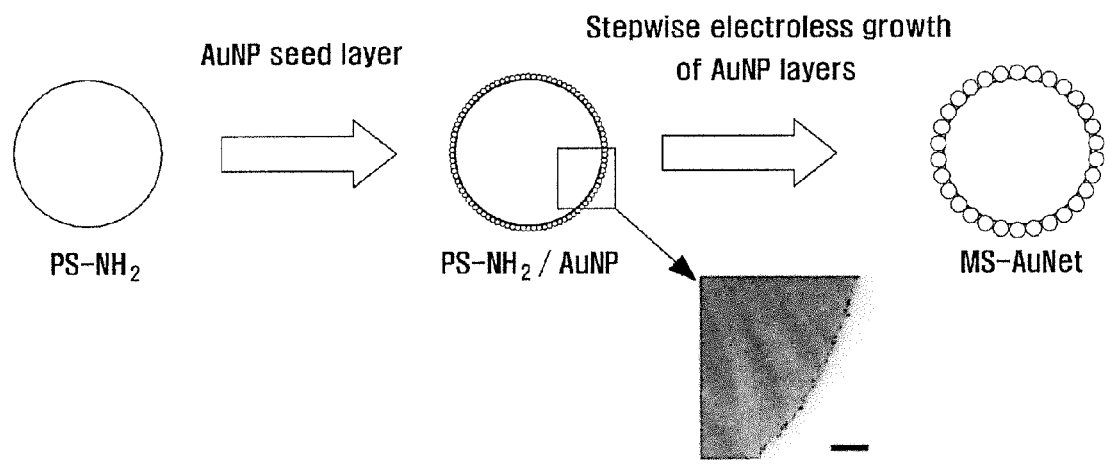
FIGS. 1a and 1b show a schematic view and a scanning electron microscopic (SEM) image of a process for preparing a gold microshell capable of electrochemical and spectroscopic monitoring.
Figure 1B:
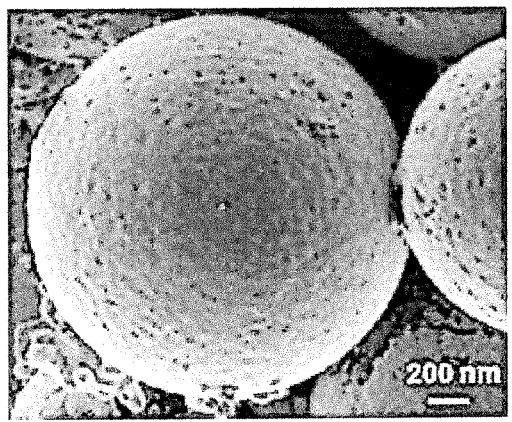
Figure 2A:
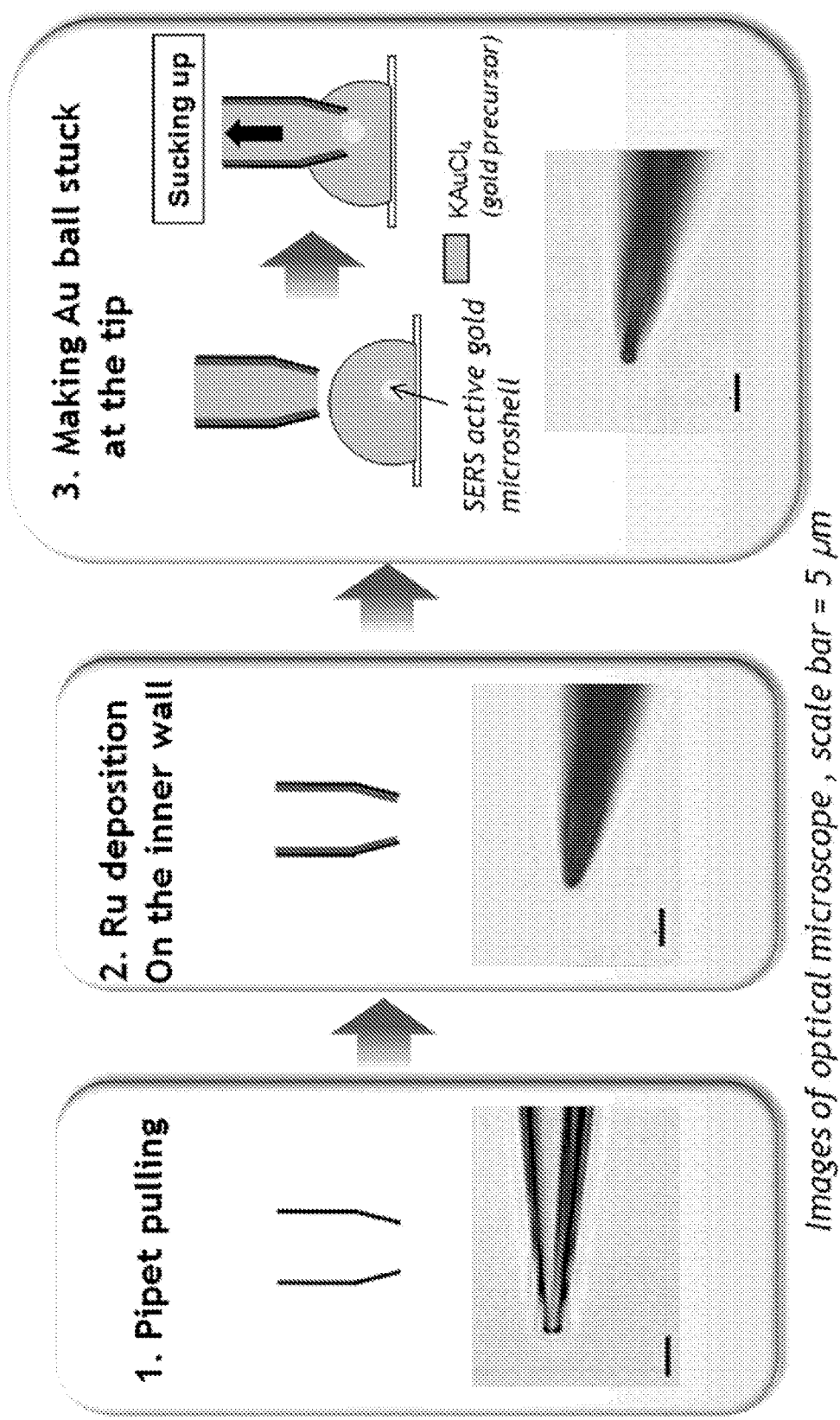
FIGS. 2a and 2b schematically describe a method for electrically connecting a gold microshell.
Figure 2B:
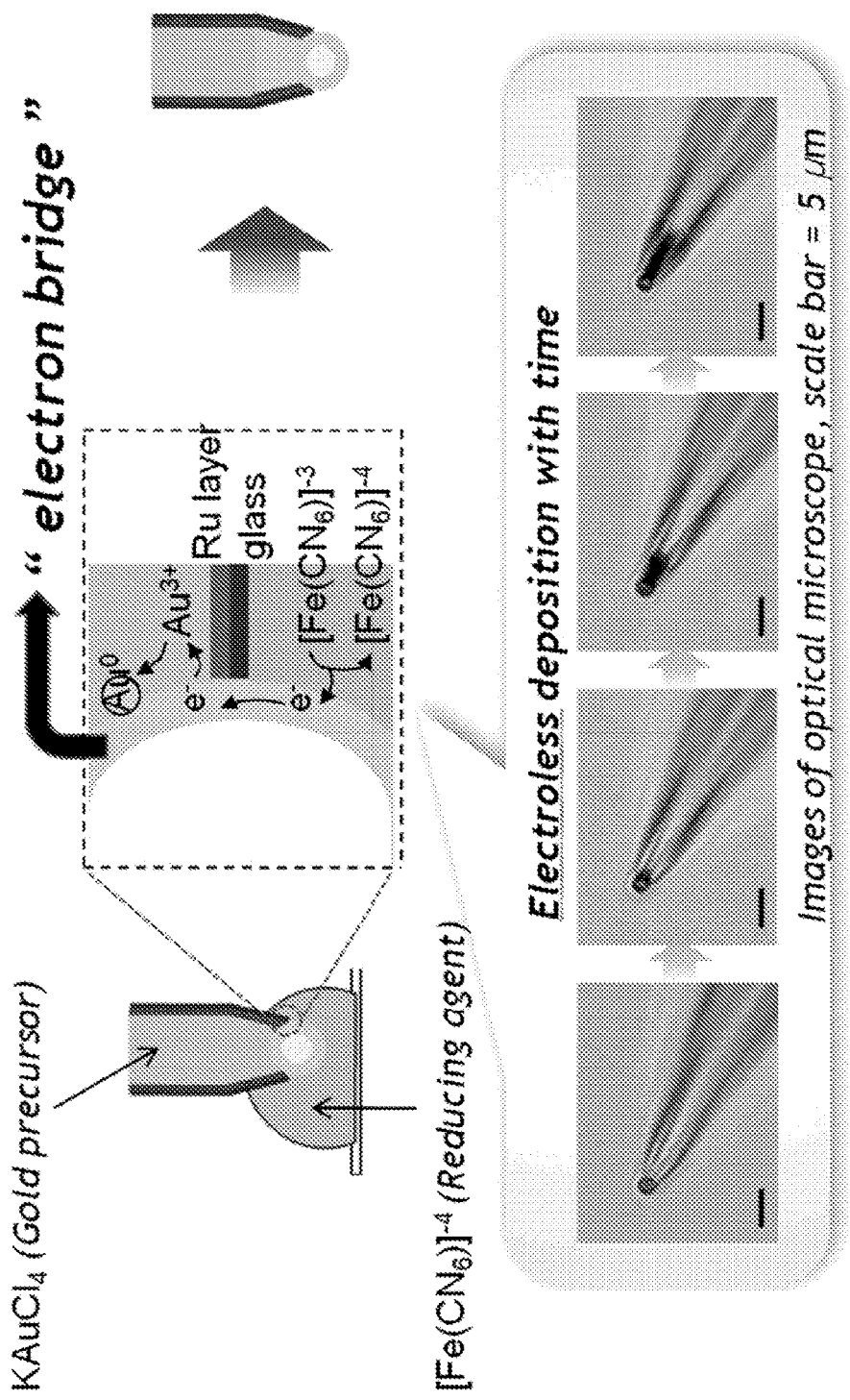
Figure 3:
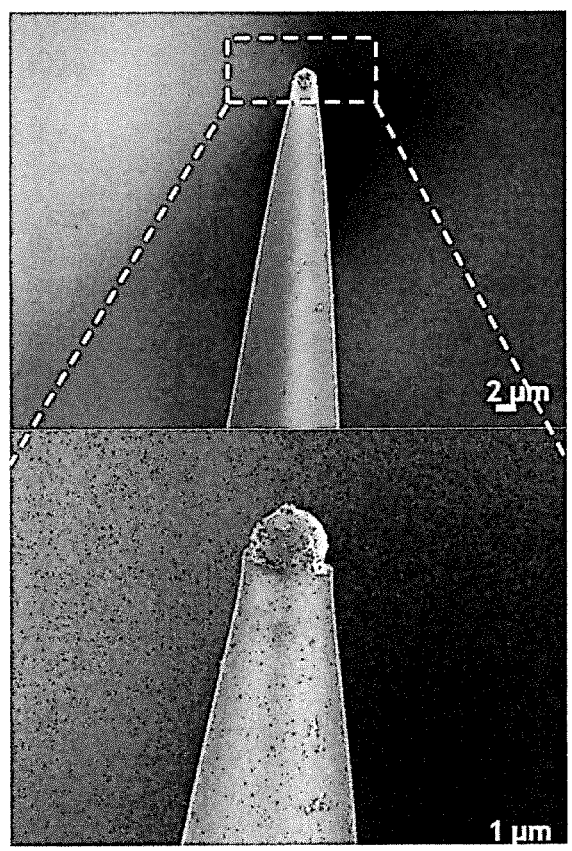
FIG. 3 is an electron microscopic image of a completed probe.
Figure 4A:
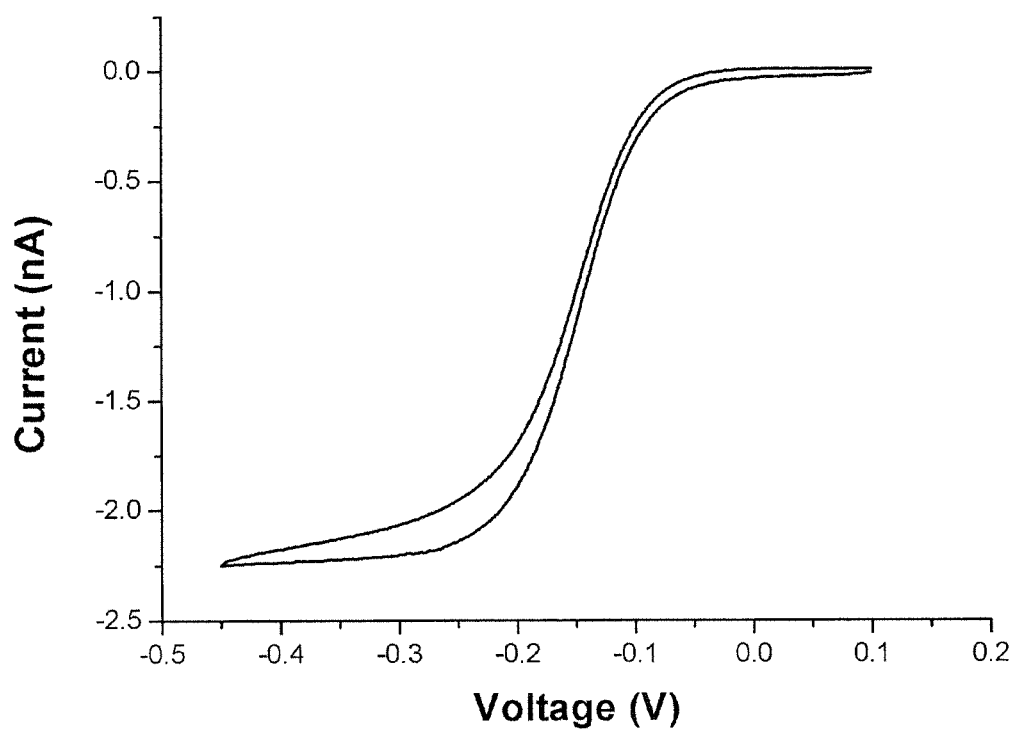
FIG. 4a shows a result of monitoring electrochemical behavior using an ultramicroelectrode and FIG. 4b shows a result of obtaining Raman spectrum of a specific molecule using a Raman probe.
Figure 4B:
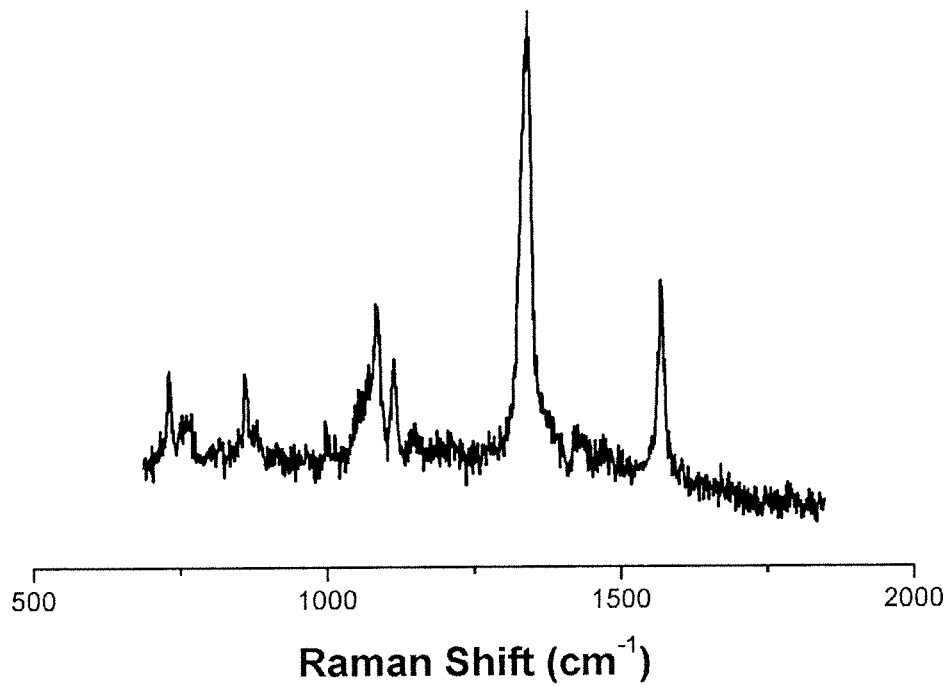
Figure 5:
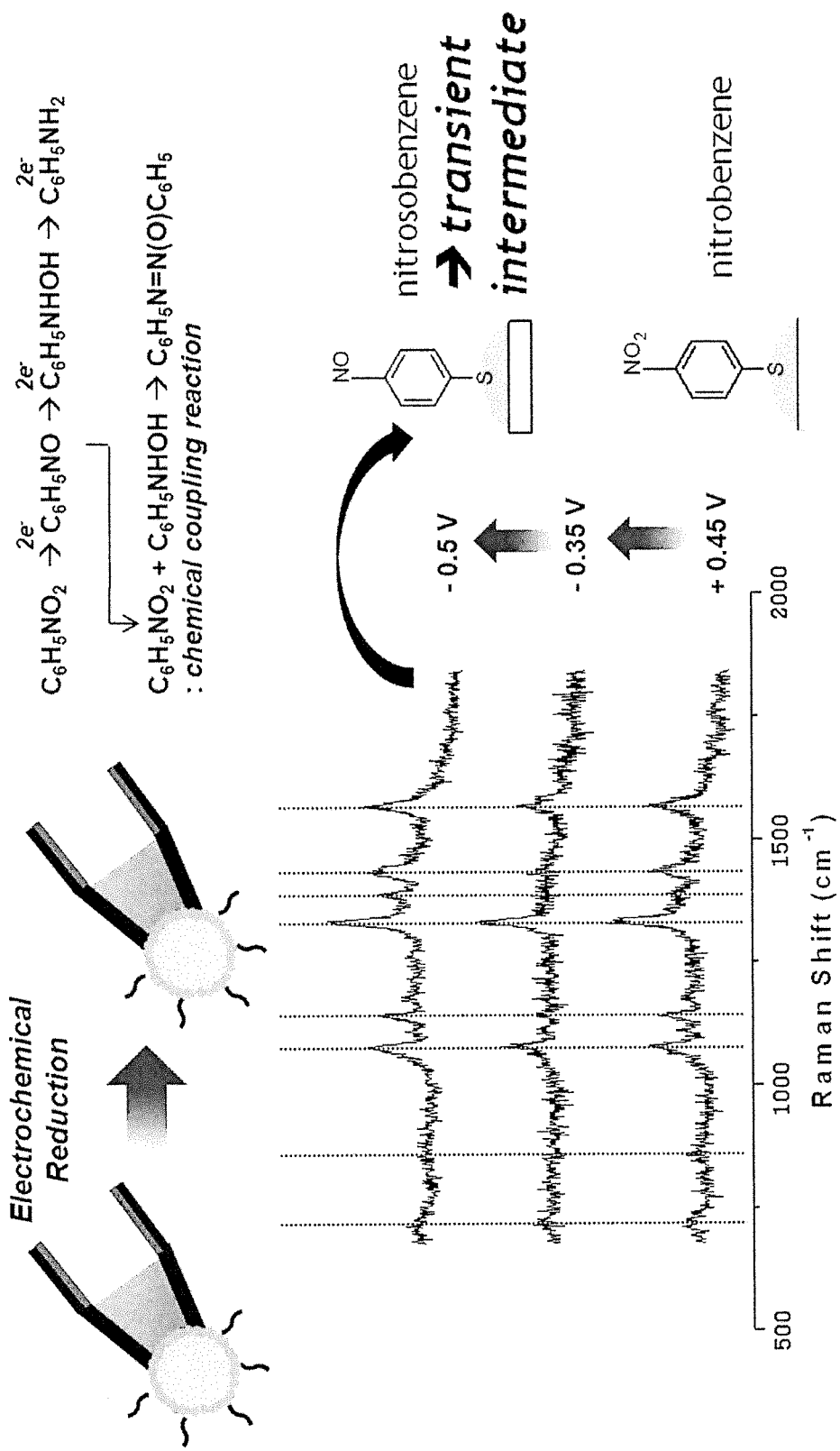
FIG. 5 shows a schematic view and an experimental result showing applicability as an electrochemical and spectroscopic probe.
Figure 6:
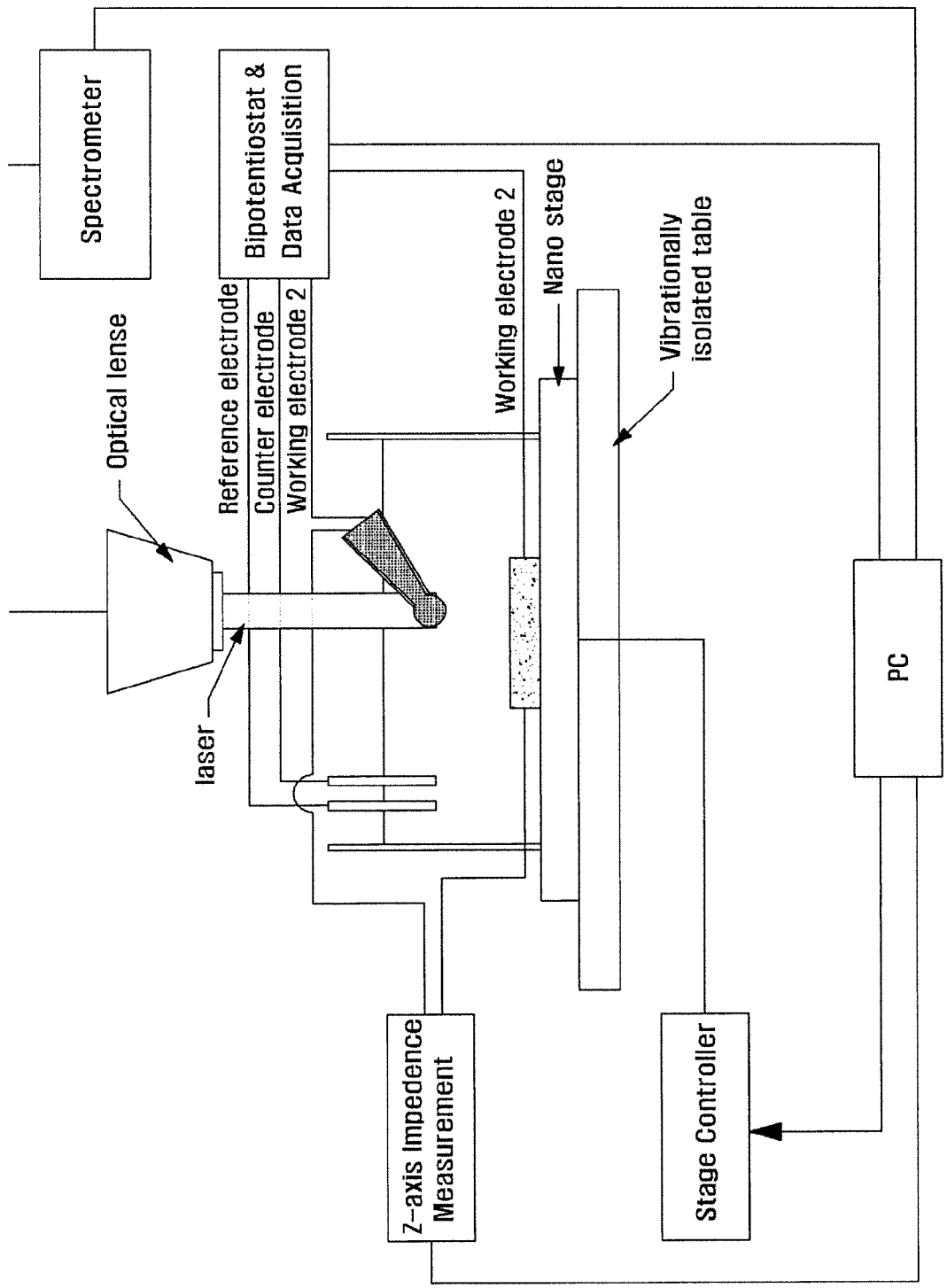
FIG. 6 shows a circuit diagram of a feedback system for precisely moving a probe not only along the x- and y-axes but also along the z-axis.

Preparation of Probe Capable of Electrochemical and Raman Spectroscopic Monitoring A gold microshell capable of electrochemical and spectroscopic monitoring was prepared by electroless plating on a microsized polymer ball as described in FIG. 1. Specifically, amine-terminated polystyrene beads (PS-$NH_2$, diameter 1.8 μm, 10% aqueous dispersion, Bangs Laboratories, Inc.) were added to a solution of colloidal gold nanoparticles (AuNPs, diameter 2-3 nm) and the mixture was shaken for 2 hours so that the gold nanoparticles were attached to the amine groups. The solution of the colloidal gold nanoparticles had been prepared by adding 2.0 mL (27 mmol) of 1% gold(III) chloride trihydrate ($HAuCl_4$, Aldrich) to a mixture of 0.5 mL of 1 M sodium hydroxide (Aldrich) solution and 1 mL of tetrakis(hydroxymethyl)phosphonium chloride (THPC, >80%, Aldrich) solution (prepared by adding 12 μL of 80% THPC (0.067 mmol) aqueous solution to 1 mL of water) and mixing until the color turned brown. The AuNPs-attached PS beads were added to an Au plating solution. After mixing well, formaldehyde (HCHO) aqueous solution (37 wt. %, Aldrich) was added as a reducing agent and reaction was performed for 2 minutes. This electroless plating process was repeated 10 times to maximize the SERS effect. The Au plating solution had been prepared by adding 15 mL of 1% $HAuCl_4$ aqueous solution to 250 mg (0.18 mmol) of potassium carbonate and mixing until the yellow solution became transparent. FIG. 1b is an electron microscopic image of thus prepared gold microshell which exhibits the highest SERS effect while maintaining conductivity since the plated gold nanoparticles are connected with each other.

An electrical connection is to be made in order to use the gold microshell as an electrode. For this, a borosilicate glass capillary tube (GC 150-7.5 Harvard Apparatus) was stretched to such a size that the gold microshell can be trapped using a laser-based micropipette puller device (Sutter Instruments Inc., P-2000) and its inner wall was coated with a conductive material. The coated conductive material was ruthenium (Ru), which exhibits much superior conductivity than graphitic carbon that has been used for similar purposes. The coating of the metallic conductive film on the inner wall of the glass microcapillary tube having a high aspect ratio was possible only by atomic layer deposition (ALD). The atomic layer deposition of ruthenium was performed at 300° C. under a pressure of 3 Torr using the GENI-MP1000 ALD system (ASM-Genitech, Inc.). Bis (ethylcylcopentadienyl)ruthenium was used as a Ru precursor. The highly conductive Ru coated on the glass microcapillary tube made of glass having excellent insulating property is ideal for providing electrical connection with the gold microshell.

Before attaching the gold microshell to the tip of the Ru-coated glass microcapillary tube, the gold microshell was trapped by applying a negative pressure. For the gold ball to be trapped in the tip of the microcapillary tube, the tip of the microcapillary tube should have an appropriate size (slightly smaller than the gold ball). For electroless plating to completely attach the gold microshell to the tip of the microcapillary tube, the trapping was performed in 1% potassium tetrachloroaurate hydrate (STREM chemicals) solution as the gold precursor.

Finally, the trapped gold microshell probe was transferred to 0.25 M potassium ferrocyanide ($K_4[Fe(CN)_6]$) (Junsei Chemical Co., Ltd.) solution as a reducing agent. This was achieved in solution since the gold shell may be detached if exposed to the air. An electron coming from reducing agent moves toward the gold precursor inside the glass microcapillary tube using the gold shell as an electron bridge and reduces the gold precursor to gold on the surface of the gold shell. The reducing agent used has an appropriate reducing ability to donate the electron to the gold shell without producing byproducts. Through the electroless plating process, gold was reduced on the surface of the gold microshell trapped inside the Ru-coated glass microcapillary tube and the reduced gold provided electrical connection to the gold microshell since it was physically connected to the Ru on the inner wall of the glass microcapillary tube.

Electrochemical and Raman Spectroscopic Monitoring Ability of Probe

The performance of the prepared probe as an ultramicroelectrode was confirmed by steady-state current exhibited in 5 mM ruthenium hexamine chloride solution (Sigma-Aldrich) in 0.1 M potassium chloride (Dae Jung). A silver-silver chloride electrode (BASi) was used as a reference electrode and a platinum wire (Sigma-Aldrich) was used as a counter electrode. Also, the performance as a Raman probe was confirmed by obtaining Raman spectrum after forming a self-assembled monolayer (SAM) of 10 mM nitrobenzene thiol (NBT) on the probe. A homemade Ramboss micro-Raman system spectrometer was used and 632.8-nm light from a 20 mW He/Ne laser (model LGK7665) was used as an excitation source. The performance as a probe capable of electrochemical and Raman spectroscopic monitoring at the same time was confirmed as follows. After attaching NBT to the probe, a voltage for reducing the NBT was applied and the reduction process of NBT was monitored with Raman spectra. By coupling the probe with a system capable of moving the probe to a desired location, the activities of various catalyst materials could be detected quickly and intermediate products attached on the surface could be imaged.

The invention claimed is:

1. A method for preparing a probe, comprising (a) preparing a metallic microshell by coating a first metallic material on the surface of a spherical template, (b) preparing a conductive capillary tube by coating a conductive material on the inner wall of a capillary tube, (c) trapping the metallic microshell in a tip of the conductive capillary tube and (d) coating a second metallic material on the inner wall of the conductive capillary tube wherein the metallic microshell is trapped.

2. The method for preparing a probe according to claim 1, wherein the template is selected from polystyrene, poly (methyl methacrylate), silica and a mixture thereof, the first metallic material is selected from Au, Ag, Pt, Pd, Cu and a mixture thereof, the conductive material is selected from Ru, Pt, Cu, Co, Ni and a mixture thereof and the second metallic material, which may be identical to or different from the first metallic material, is selected from Au, Ag, Pt, Pd, Cu and a mixture thereof.

3. The method for preparing a probe according to claim 1, wherein the metallic microshell has a diameter of 1-3 μm and the tip of the capillary tube has a diameter corresponding to 50-99% of the diameter of the metallic microshell.

4. The method for preparing a probe according to claim 1, wherein (a) is performed by electroless plating using (i) a precursor of the first metallic material selected from potassium tetrachloroaurate hydrate, sodium tetrachloroaurate hydrate, chloroauric acid, hydrogen hexachloroplatinate(IV) hydrate, silver nitrate and a mixture thereof and (ii) a first reducing agent selected from formaldehyde, ascorbic acid, hydroquinone, ammonium hydroxide and a mixture thereof.

5. The method for preparing a probe according to claim 4, wherein (a) is performed by repeating the electroless plating 2-20 times such that SERS activity and Raman effect can be maximized.

6. The method for preparing a probe according to claim 1, wherein (b) is performed by atomic layer deposition at 250-350° C. under a pressure of 1-5 Torr using a precursor selected from bis(ethylcylcopentadienyl)ruthenium, a halide compound of the conductive material, an alkyl or alkoxide compound of the conductive material, an organometallic compound such as a cyclopentadienyl complex or an alkyl or silyl amide and a mixture thereof.

7. The method for preparing a probe according to claim 1, wherein (c) is performed by applying a negative pressure to the capillary tube.

8. The method for preparing a probe according to claim 7, wherein (c) is performed in a solution of a precursor of the second metallic material selected from potassium tetrachloroaurate hydrate, sodium tetrachloroaurate hydrate, chloroauric acid, hydrogen hexachloroplatinate(IV) hydrate and a mixture thereof and a part of the solution of the precursor of the second metallic material is sucked into the capillary tube.

9. The method for preparing a probe according to claim 1, wherein (d) is performed by electroless plating using (i) a precursor of the second metallic material selected from potassium tetrachloroaurate hydrate, sodium tetrachloroaurate hydrate, chloroauric acid, hydrogen hexachloroplatinate(IV) hydrate and a mixture thereof and (ii) a second reducing agent selected from potassium ferrocyanide ($K_4[Fe(CN)_6]$), ruthenium(II) hexamine chloride, iridium(III) chloride and a mixture thereof.

10. The method for preparing a probe according to claim 9, wherein (d) is performed in a solution of the second reducing agent.

11. The method for preparing a probe according to claim 7 or 9, which further comprises, between (c) and (d), (c-1) diluting the solution of the precursor of the first metallic material and (c-2) adding a second reducing agent or a solution thereof to the diluted solution of the precursor of the first metallic material, wherein all of (c), (c-1), (c-2) and (d) are performed with the capillary tube in a solution.

12. A probe comprising (i) a capillary tube and (ii) a metallic microshell attached to a tip of the capillary tube, wherein
a conductive material is coated on the inner wall of the capillary tube,
the metallic microshell comprises a first metallic material coated on the surface of a spherical template,
a second metallic material is coated on a layer of the first metallic material of the metallic microshell, which is exposed in the tip of the capillary tube to which the metallic microshell is attached, and
the conductive material and the first metallic material are electrically connected.

13. The probe according to claim 12, wherein the template is selected from polystyrene, poly(methyl methacrylate), silica and a mixture thereof, the first metallic material is selected from Au, Ag, Pt, Pd, Cu and a mixture thereof, the conductive material is selected from Ru, Pt, Cu, Co, Ni and a mixture thereof and the second metallic material is selected from Au, Ag, Pt, Pd, Cu and a mixture thereof.

14. The probe according to claim 12, wherein the metallic microshell has a diameter of 1-3 μm and the tip of the capillary tube has a diameter corresponding to 50-99% of the diameter of the metallic microshell.

15. The probe according to claim 12, wherein the first metallic material is coated on the spherical template such that SERS activity and Raman effect can be maximized.

16. The probe according to claim 13, wherein the first metallic material is coated on the spherical template by repeating electroless plating 2-10 times such that SERS activity and Raman effect can be maximized.

17. A probe comprising:
(i) a capillary tube comprising a conductive material inside thereof;
(ii) a metallic microshell comprising a first metallic material coated on the surface of a spherical template and attached to a tip of the capillary tube; and
(iii) a second metallic material disposed between the capillary tube and the metallic microshell,
wherein the conductive material and the first metallic material are electrically connected via the second metallic material.

18. The probe according to claim 17, wherein the capillary tube comprising the conductive material is prepared by pulling a glass tube comprising a metal wire.

19. A method for preparing a probe, comprising:
(a) preparing a metallic microshell by coating a first metallic material on the surface of a spherical template;
(b) preparing a capillary tube comprising a conductive material inside thereof;
(c) insert a second metallic material into a tip of the capillary tube; and
(d) attaching the metallic microshell to a tip of the capillary tube through the second metallic material.

20. The method for preparing a probe according to claim 6, wherein the halide compound is a chloride compound.

* * * * *